United States Patent
Foley (10) Patent No.: US 9,068,922 B2
(45) Date of Patent: Jun. 30, 2015

(54) ESTIMATING COOLANT CONDUCTIVITY IN A MULTI-VOLTAGE FUEL CELL SYSTEM

(71) Applicant: GM Global Technology Operations LLC, Detroit, MI (US)

(72) Inventor: Robert S. Foley, Rochester, NY (US)

(73) Assignee: GM Global Technology Operations LLC, Detroit, MI (US)

( * ) Notice: Subject to any disclaimer, the term of this patent is extended or adjusted under 35 U.S.C. 154(b) by 361 days.

(21) Appl. No.: 13/832,135

(22) Filed: Mar. 15, 2013

(65) Prior Publication Data

US 2014/0266223 A1 Sep. 18, 2014

(51) Int. Cl.
  *G01N 27/02* (2006.01)
  *G01N 27/06* (2006.01)
  *H01M 8/04* (2006.01)

(52) U.S. Cl.
  CPC ............ *G01N 27/06* (2013.01); *H01M 8/04559* (2013.01); *Y02E 60/50* (2013.01); *H01M 8/04962* (2013.01); *H01M 8/04992* (2013.01); *H01M 8/04813* (2013.01); *H01M 2250/20* (2013.01)

(58) Field of Classification Search
  CPC ....... H02J 7/0093; H02J 7/045; H01M 10/44; Y02E 60/12; Y02E 60/122
  USPC .......................................................... 324/432
  See application file for complete search history.

(56) References Cited

U.S. PATENT DOCUMENTS

| | | | |
|---|---|---|---|
| 6,582,840 B2 | 6/2003 | Hortop | |
| 6,838,201 B2 | 1/2005 | Dill | |
| 7,906,242 B2 | 3/2011 | Raiser | |
| 2004/0265660 A1* | 12/2004 | Reuschel et al. | 429/26 |
| 2005/0274676 A1* | 12/2005 | Kumar et al. | 210/681 |
| 2006/0188068 A1* | 8/2006 | Anno et al. | 378/130 |
| 2009/0226769 A1* | 9/2009 | Ota | 429/13 |
| 2012/0064426 A1* | 3/2012 | Sato et al. | 429/434 |

* cited by examiner

Primary Examiner — Arun Williams
(74) Attorney, Agent, or Firm — Dinsmore & Shohl LLP (57) ABSTRACT

A coolant conductivity method and apparatus used to determine when a coolant, circulating through a vehicle's coolant system, starts to conduct electrical current and loses its electrical isolation properties. The system includes a battery monitor controller senses one or more isolation resistances placed throughout a fuel cell system and is programmed to run an isolation algorithm. The isolation algorithm opens and closes contactors in a specific order, measures the resistance of the one or more isolation resistances and calculates a coolant conductivity value. The system will indicate when the coolant needs to be replaced.

20 Claims, 6 Drawing Sheets

ESTIMATING COOLANT CONDUCTIVITY IN A MULTI-VOLTAGE FUEL CELL SYSTEM

BACKGROUND

The present disclosure relates generally to a system and method to monitor the isolation resistance in a fuel cell system and more particularly to estimate the coolant conductivity circulating in the fuel cell system.

Current fuel cell technology requires a low conductivity (high resistance) coolant to prevent leakage current from flowing between the stack in the remainder of the system. Leakage current flowing through the coolant can cause short circuiting, induce galvanic corrosion and electrolyze the coolant, reducing engine efficiency. Generally non-corrosive coolants such as water, antifreeze, or mixtures thereof, etc., are used in the bipolar plates. Over time, however, the internal heat exchange faces of the bipolar plates begin to dissolve. As the coolant ages it collects contaminants that cause it to become electrically conductive such that the stack coolant could conduct a leakage current throughout the coolant loop.

Electrical isolation resistance monitoring is required for many fuel cell automotive systems. Typically, the isolation resistance is monitored on the propulsion high voltage bus. If the fuel cell stack is interfaced to the propulsion bus through a voltage converter, its isolation resistance is scaled by some function of the converter's voltage gain. The exact function is dependent on the converter type and which high voltage rail, positive or negative, is common to the system.

A general isolation fault requires that a service technician isolate components from the high voltage bus one-by-one to isolate if the root cause of the isolation fault is the coolant. This is undesirable because of the time and labor needed to track down the cause of the fault. Accordingly, a need exists for alternative methods to determine if coolant conductivity is excessively high and the cause of the fault.

SUMMARY

In one embodiment, a method for monitoring coolant conductivity in a coolant system that used to provide thermal management of a fuel cell stack may include closing at least one contactor in an electrical system comprising a stack voltage and a battery voltage, measuring a first isolation value, a second isolation value, the stack voltage, and the battery voltage, opening the at least one contactor in the electrical system, measuring a first negative isolation value, calculating a stack isolation resistance using the first isolation value, the second isolation value, the first negative isolation value, the stack voltage, and the battery voltage, calculating a coolant conductivity value, and providing indicia that the coolant needs to be replaced when the coolant conductivity value crosses a threshold value.

In another embodiment, method for monitoring the isolation resistance in a vehicular propulsion system may include circulating a coolant in a coolant system fluidly coupled to a fuel cell stack that forms at least a portion of the propulsion system wherein the coolant provides thermal management within the fuel cell stack and the coolant provides electrical isolation between the fuel cell stack and a vehicle chassis, measuring a first isolation value, a second isolation value, the stack voltage, and the battery voltage, opening the at least one contactor in the electrical system, measuring a first negative isolation value, calculating a stack isolation resistance using the first isolation value, the second isolation value, the first negative isolation value, the stack voltage, and the battery voltage, calculating a coolant conductivity value, and indicating the coolant in the coolant system needs to be replaced with the coolant conductivity value crosses a threshold value.

In yet another embodiment, a coolant conductivity estimation system for a fuel cell may include a plurality of isolation sensors and a battery monitor controller. The plurality of isolation sensors include a first isolation sensor electrically coupled to a positive stack isolation resistance measurement location and used to measure the first isolation value, a second isolation sensor electrically coupled to a positive battery isolation resistance measurement location and used to measure the second isolation value, a plurality of negative sensors are electrically coupled to a negative stack isolation resistance measurement location, and a negative battery isolation resistance measurement location and used to measure the first negative isolation value, a stack sensor used to measure the stack voltage, and a battery sensor used to measure the battery voltage. The battery monitor controller is electrically coupled to the plurality of isolation sensors and include a processor and a computer-readable medium and executing an isolation algorithm, the isolation algorithm includes closing at least one contactor in an electrical system comprising a stack voltage and a battery voltage, measuring a first isolation value, a second isolation value, the stack voltage, and the battery voltage, opening the at least one contactor in the electrical system, measuring a first negative isolation value, calculating a stack isolation resistance using the first isolation value, the second isolation value, the first negative isolation value, the stack voltage, and the battery voltage, calculating a coolant conductivity value, and providing indicia that the coolant needs to be replaced when the coolant conductivity value crosses a threshold value.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The present disclosure does not rely on a separate and distinct coolant conductivity sensor to determine a conductivity of a coolant running through a cooling system of a fuel cell system. The present disclosure utilizes measurements from sensors monitoring a multi-voltage system to determine the coolant conductivity of the coolant without the need for the coolant conductivity sensor.

Figure 1:
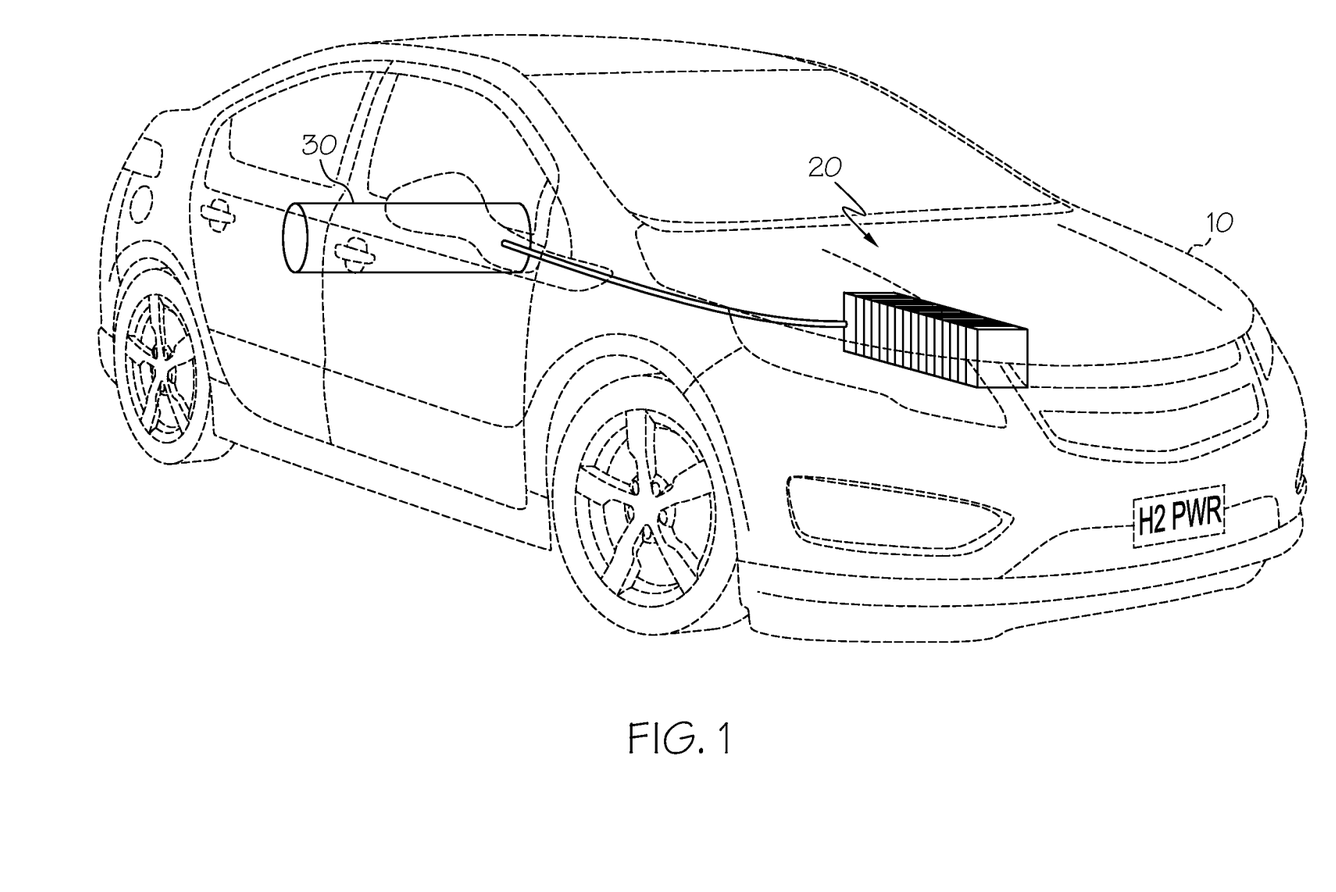
FIG. 1 depicts a vehicle with a fuel cell system according to one or more embodiments shown and described herein.

FIG. 1 depicts a vehicle 10 (e.g., a car, bus, truck, or motorcycle) powered by a fuel cell system. Some components of the fuel cell system may include numerous fuel cells (preferably arranged as one or more stacks 20) that convert stored gaseous fuel from a tank 30 into electricity to provide electric power to engine (not shown) that may be a fully electric or a hybrid electric engine (e.g., an engine that uses both electricity and petroleum-based combustion for propulsion power), utilizes the power from the fuel cell system to propel vehicle 10. The fuel cell system may also include any number of valves, compressors, tubing, temperature regulators, electrical storage devices (e.g., batteries, ultra-capacitors or the like), and controllers to deliver the fuel from the tank 30 or tanks to the fuel cell system, as well as to provide control over the operation of fuel cell system. Such controllers will be discussed in more detail below.

Any number of different types of fuel cells may be used in the fuel cell system (e.g., metal hydride fuel cells, alkaline fuel cells, electrogalvanic fuel cells, or any other type of known fuel cells). Multiple fuel cells may also be combined in series and/or parallel within the fuel cell system as the stack 20 in order to produce a higher voltage and/or current yield by the fuel cell system. The produced electrical power may be supplied directly to an engine (not shown) or stored within an electrical storage device (not shown) for later use by vehicle 10.

A coolant is circulated in a coolant system fluidly coupled to the fuel cell stack 20 that forms at least a portion of a vehicular propulsion system. The coolant provides thermal management within the fuel cell stack 20, as well as electrical isolation between the fuel cell stack 20 and a vehicle 10 chassis.

Figure 2:
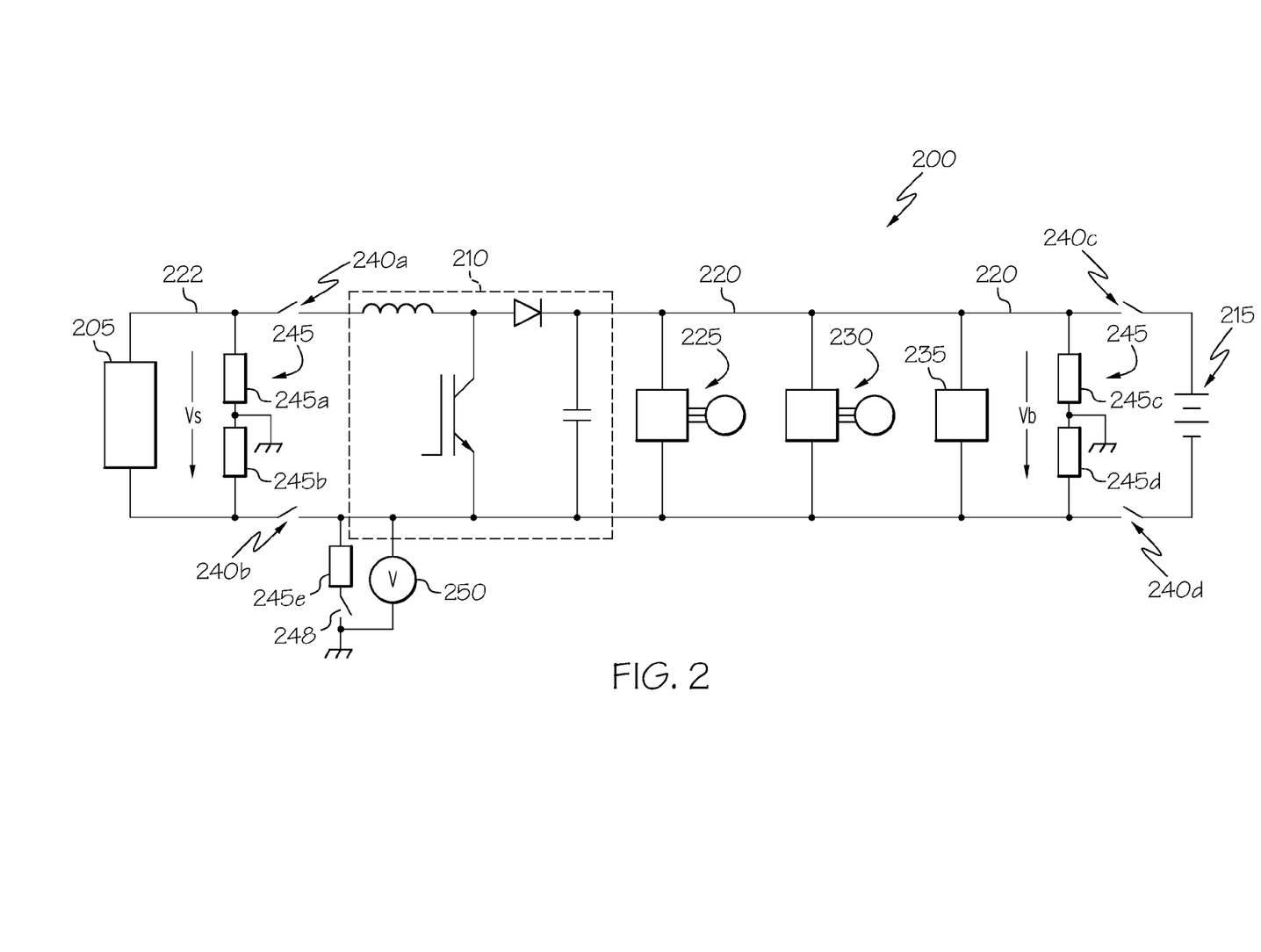
FIG. 2 illustrates a multi-voltage architecture of the fuel cell system according to one or more embodiments shown and described herein.

FIG. 2 illustrates the multi-voltage architecture of a fuel cell system 200. The fuel cell stack 205, a boost converter 210, and a high voltage battery 215 are electrically coupled via a stack bus 222 and a propulsion bus 220. The fuel cell stack 205 provides electric power to a variety of vehicle 10 systems to include but not limited to a compressor motor 225, a traction motor 230, and other loads 235 which may include control systems, a high temperature pump, a radiator fan, and a cabin heater. There are at least one contactor 240 that are electrically coupled to the propulsion bus 220 and may provide electrical isolation of the vehicle 10 systems from the sources of electrical power which may include the fuel cell stack 205 and the high voltage battery 215. One or more isolation resistance measurement locations 245 may be found at various locations within the fuel cell system 200. The one or more isolation resistance measurement locations 245 may be a resistor and/or an impedance element of a defined and know resistive or impedance value which may be dependent on the voltages of the fuel cell system 200 and sensitivity of a one or more measurement sensor used to detect their values. Furthermore, the one or more isolation resistance measurement locations 245 may also be terminals to which the one or more sensors are connected.

In some embodiments, there may be four isolation resistance measurement locations 245a-d found on the positive and negative terminals both the fuel cell stack 205 and the high voltage battery 215. A positive stack isolation resistance measurement location 245a is electrically coupled to a positive terminal of the fuel cell stack 205 and ground. A negative stack isolation resistance measurement location 245b is electrically coupled to a negative terminal of the fuel cell stack 205 and ground. A positive battery isolation resistance measurement location 245c is electrically coupled to a positive battery terminal of the high voltage battery 215 and ground. A negative battery isolation resistance measurement location 245d is electrically coupled to a negative battery terminal of the high voltage battery 215 and ground. Ground as used throughout this application means a common reference point from which electrical measurements are taken and/or a common return path for electrical current to a power source. Ground, as used throughout this disclosure, may also be labelled as a chassis or a chassis ground.

A bus isolation resistance measurement location 245e may be electrically coupled to the propulsion bus 220 and ground. The bus isolation resistance measurement location 245e may allow for a measurement of the isolation of the propulsion bus 220 from the rest of the vehicle 10. In parallel with the bus isolation resistance measurement location 245e is a voltage measurement location 250. The voltage measurement location 250 may allow for a sensed voltage value of the bus as it relates to ground. A switch 248 electrically isolates the bus isolation resistance measurement location 245e. In one embodiment, a method to determine a coolant conductivity value would involved measuring the voltage value from the voltage measurement location 250, closing the switch 248, and taking another voltage value from the voltage measurement location 250 and compare the two voltage values. Through the comparison, as known in the art, the coolant conductivity value may be determined. The coolant conductivity value from this embodiment may be used to compare against the coolant conductivity value resulting from other embodiments of this disclosure.

In some embodiments, the at least one contactor 240 may be grouped together to allow for the measurement of the isolation resistance measurement locations 245a-e. For example, at least one contactor 240a and 240b may be grouped together and labeled a stack contactors and at least one contactor 240c and 240d may be grouped together and labeled a battery contactor. In addition to falling under a common label, the grouped contactors may also be actuated together (i.e. opened together and closed together).

The boost converter 210 changes the electrical potential between the fuel cell stack 205 and the high voltage battery 215. This necessitates the one or more isolation resistance measurement locations 245 within the fuel cell system 200 as the electrical potential on the fuel cell stack 205 side (left) of the boost converter 210 may be an several times lower than the high voltage battery 215 side (right) of the boost converter 210. In some embodiments, Vs is greater in electrical potential than Vb. The boost converter would be a buck converter in this embodiment and the calculations for coolant conductivity would be the same.

Figure 3:
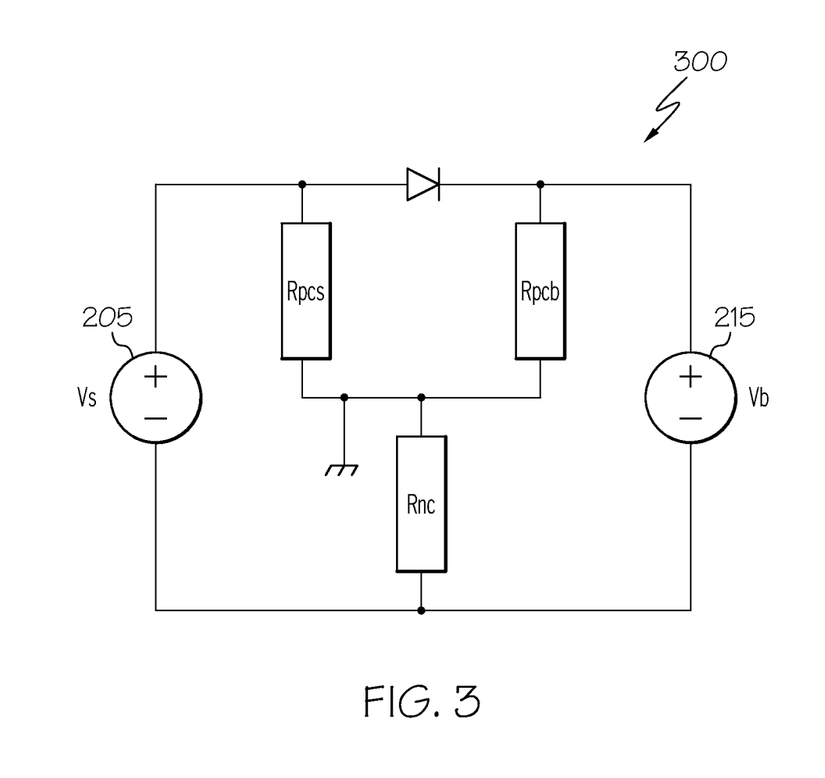
FIG. 3 illustrates an isolation resistance model the fuel cell system according to one or more embodiments shown and described herein.

FIG. 3 illustrates the fuel cell system 200 of FIG. 2 as an isolation resistance model 300. Vs represents the voltage of the fuel cell stack 205. Vb represents the voltage of the high voltage battery 215. Rpcs represents the parallel combination of all resistance connected from the fuel cell stack 205 positive terminal to ground and may include the positive stack isolation resistance measurement location 245a. Rpcb represents the parallel combination of all resistances connected from the battery positive terminal to ground and may include the positive battery isolation resistance measurement location 245c. Rnc represents the parallel combination of all resistances connected from the shared negative terminal to ground and may include the negative stack isolation resistance measurement location 245b and the negative battery isolation resistance measurement location 245d. In an operating fuel cell system 200, Vb may be greater than Vs as explained above in regards to the boost converter 210. The purpose of the isolation resistance is to limit current through unintended connections between the propulsion bus 220 and ground. The isolation resistance model 300 represents three possible paths from the propulsion bus 220 to ground. $Rpc_{PB}$ is calculated using Eqn. 1 with the stack contactors 240*a-b* and battery contactors 240*c-d* closed:

$$Rpc_{PB} = \left(\frac{Vb}{Vs}\right) \cdot Rpcs \,//\, Rpcb \qquad \text{Eqn. 1}$$

$Rnc_{PB}$ is calculated using Eqn. 2 with the stack contactors 240*a-b* and battery contactors 240*c-d* closed:

$$Rnc_{PB} = \left(\frac{Vb}{Vb - Vs}\right) \cdot Rpcs \,//\, Rnc \qquad \text{Eqn. 2}$$

Rpcs is calculated using Eqn. 3 with the stack contactors 240*a-b* open and the battery contactors 240*c-d* closed:

$$Rpcs = \frac{Rpcb \cdot Rpc_{PB} \cdot Vs}{Rpcb \cdot Vb - Rpc_{PB} \cdot Vb} \qquad \text{Eqn. 3}$$

$Rpc_{PB}$ is the apparent positive to chassis isolation resistance measured on the propulsion bus 220. $Rnc_{PB}$ is the apparent negative to chassis isolation resistance measured on the propulsion bus 220. Rpcs is the fuel cell stack 205 coolant positive to chassis isolation resistance. Rpcb is the propulsion bus 220 positive to chassis isolation resistance and Rnc is the propulsion bus negative to chassis isolation resistance. "//" is a shorthand notation for parallel where R1//R2=1/(1/R1+1/R2).

For example, if the fuel cell system 200 was a single voltage system, Eqn. 1 would be Rpcs//Rpcb as two sets of isolation resistances would be subject to the same voltage. In the present disclosure, a multi-voltage system is present with a boost converter 210 and possibly a second boost converter 505 as shown below in FIG. 5. The isolation resistance found in the fuel cell system 200 is subject to varied voltages depending on where you are taking the voltage measurement from. To ensure that the coolant conductivity calculation is accurate, a ratio (Vb/Vs) needs to be taken into account, resulting in Eqn. 1 and subsequent Eqns. 2, 3, and 5-7.

Figure 4:
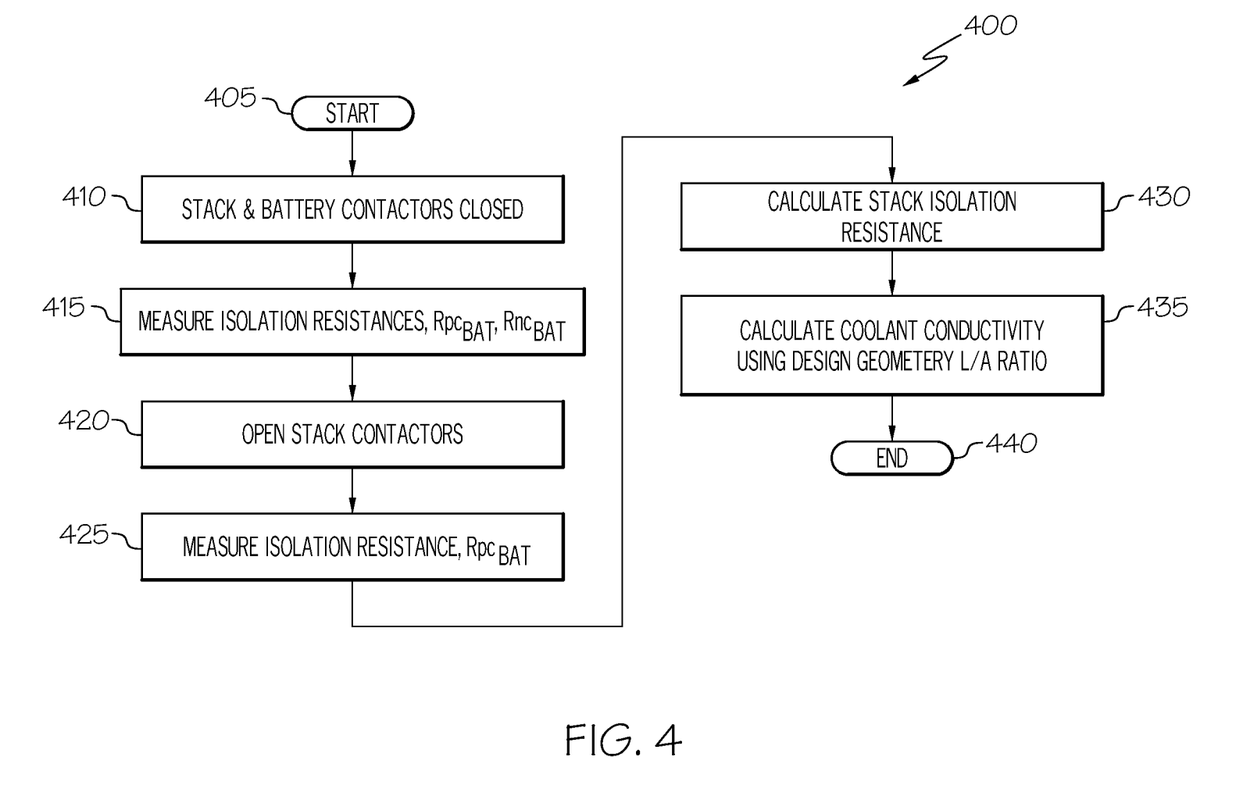
FIG. 4 depicts illustrates the procedure for estimating coolant conductivity according to one or more embodiments shown and described herein.

FIG. 4 illustrates the procedure for estimating coolant conductivity. The estimation may occur when the vehicle 10 of FIG. 1 is first starting up from a shut down state or when the vehicle 10 is in the process of shutting down. A battery monitor controller may be used to execute an isolation algorithm 400 or the isolation algorithm 400 may be executed in a vehicle control module such as, for example, an on-board control module (OCM) or a battery module. The battery monitor controller or the vehicle control module has a processor and a computer-readable medium used to execute the isolation algorithm 400. The isolation algorithm 400 starts 405 by confirming that at least one contactor 240 in FIG. 2 are closed 410. The battery monitor controller may confirm the status of the at least one contactor 240 through electrical communication with one or more vehicle control modules. For example, the battery monitor controller may be electrically coupled to the OCM where the OCM signally indicates the status of the at least one contactor 240 of the at least one contactor 240. If the at least one contactor 240 is not closed, the battery monitor controller may signally communicate that the at least one contactor 240 should close. In this embodiment, the isolation algorithm 400 may either confirm or signally communicate the stack contactor and the battery contactor to close 410.

The isolation algorithm may then measure the one or more fuel cell system 200 values through a plurality of sensors electrically coupled to the fuel cell system 200. The battery monitor controller may be electrically coupled to the plurality of sensors or a vehicle module may be electrically coupled to the plurality of sensors and the battery monitor controller may be electrically coupled to the vehicle module to get the sensed values from the plurality of sensors. The plurality of sensors may include one or more isolation sensors at the one or more isolation resistance measurement locations 245 found throughout the fuel cell system 200, a stack sensor, and a battery sensor. In one embodiment, referring to the one or more isolation resistance measurement locations 245: a first isolation value may be sensed by a first isolation sensor electrically coupled at the positive stack isolation resistance measurement location 245*a*; a second isolation value may be sensed by a second isolation sensor electrically coupled at the positive battery isolation resistance measurement location 245*c*; and a first negative isolation value may include one or more negative isolation sensors electrically coupled to the negative stack isolation resistance measurement location 245*b*, and the negative battery isolation resistance measurement location 245*d*. The first negative isolation value may be the parallel resistance measurement of the negative stack isolation resistance measurement location 245*b*, and the negative battery isolation resistance measurement location 245*d*. Rnc equates to the first negative isolation value as shown in the isolation resistance model 300 of FIG. 3.

Figure 5:
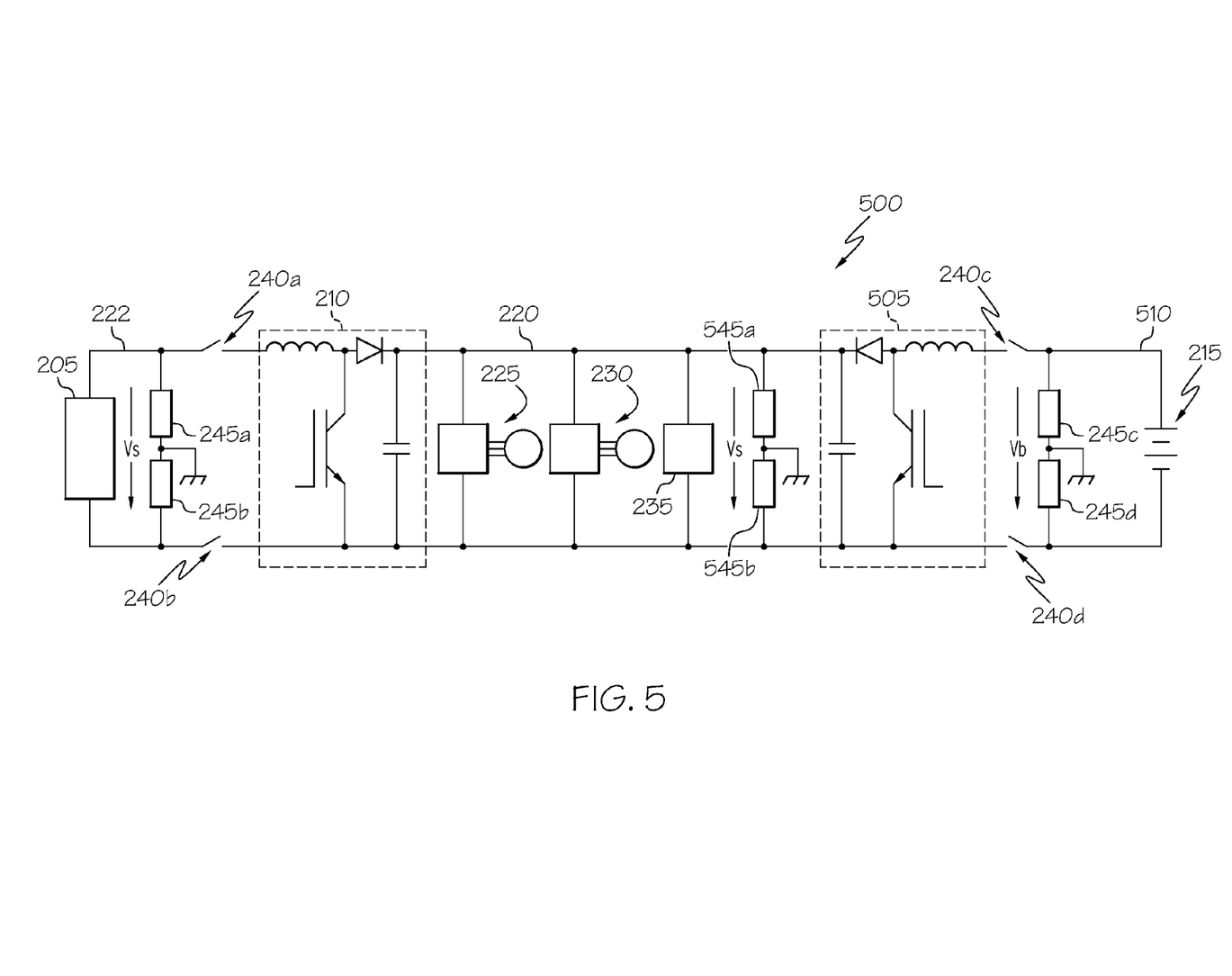
FIG. 5 illustrates a multi-voltage fuel cell system.

The stack sensor may provide a stack voltage may be sensed by the stack sensor electrically coupled between the positive and negative terminals of the stack bus 222 and a battery voltage may be sensed by the battery sensor electrically coupled between the positive and negative terminals of the battery bus 510 as shown in FIG. 5. Depending on the number of booster converters (210, 505) the propulsion bus 220 may be the same as the battery bus 510. In yet another embodiment, the isolation algorithm 400 may be executed in the OCM which is electrically coupled to the plurality of sensors negating the need for the battery management controller.

The next step for the isolation algorithm 400 is to measure 415 and or receive the first isolation value, the second isolation value, the stack voltage, and the battery voltage. The isolation algorithm 400 may then open 420 the at least one contactor 240. If, for example, the isolation algorithm 400 is executed in the battery monitor controller, the battery monitor controller may signal to a separate and distinct vehicle control module to open the at least one contactor 240 or the battery monitor controller may be electrically coupled to the at least one contactor 240 and signal for them to open 420 directly. If the isolation algorithm 400 is executed in the OCM, the OCM would signal for the at least one contactor 240 to open 420. In this embodiment, the at least one contactor 240 are the stack contactors which are signalled to open 420.

Once the stack contactors are open 420, the isolation algorithm 400 may measure 425 the first negative isolation value. The isolation algorithm 400 may then calculate a stack isolation resistance 430 using Eqn. 3 and may then calculate a coolant conductivity value 435 using Eqn. 4 that is indicative of an electrical current leakage in a coolant flowing through a coolant path in a coolant system of the fuel cell system 200. Eqn. 4 is the coolant conductivity 435 equation.

$$\sigma = \frac{1}{Rpcs} \cdot \frac{L}{A} \qquad \text{Eqn. 4}$$

Where σ is the coolant conductivity, Rpcs is the positive stack isolation resistance measurement location 245a, L is the equivalent length of the coolant path and A is the equivalent cross-sectional area of the coolant path.

The isolation algorithm 400 may provide an indicia 440 that the coolant needs to be replaced when the coolant conductivity value 435 crosses a threshold value. The coolant path geometry, represented by L and A in Eqn. 4 are design dependent as are the relative apportionment of the one or more isolation resistance measurement locations. For a particular design, an appropriate threshold value is determined using those design parameters. Indicia 440 may include a light on a dashboard of the vehicle for the user to see, an audible alarm, or a code in an on-board diagnostic system to be reported. Indicia may include any means to report that the coolant in the coolant system is conducting electrical current in the fuel cell system 200.

FIG. 5 illustrates another embodiment of a multi-voltage fuel cell system 500. The multi-voltage fuel cell system 500 includes the FIG. 2 embodiment where two or more voltages are present with the fuel cell system 200. The number of differing voltages present in the multi-voltage fuel cell system 500 depends on the number of boost converters (210, 505) present. In this embodiment found in FIG. 5, the multi-voltage fuel cell system 500 is comparable to the fuel cell system 200 found in FIG. 2 with a second boost converter 505 connecting the propulsion bus 220 and a battery bus 510. The second boost converter 505 may allow the high voltage battery 215 to be at a different electrical potential than the propulsion bus 220 and the fuel cell stack 205. The positive propulsion bus resistance measurement location 545a is electrically coupled to a positive side of the propulsion bus 220 and ground and the negative propulsion bus resistance measurement location 545b is electrically coupled to a negative side of the propulsion bus 220 and ground.

The coolant conductivity value is calculated using the following equations and Eqn. 4 above. The positive to chassis isolation resistance as measured from the propulsion bus 220 with the stack contactors 240a-b and battery contactors 240c-d closed is calculated using Eqn. 5:

$$Rpc_{PB} = \left(\frac{Vp}{Vs}\right) \cdot Rpcs \; // \; \left(\frac{Vp}{Vb}\right) \cdot Rpcb \; // \; Rpcp \qquad \text{Eqn. 5}$$

The negative to chassis isolation resistance as measured from the propulsion bus 220 with the stack contactors 240a-b and battery contactors 240c-d closed is calculated using Eqn. 6:

$$Rnc_{PB} = Rpcs \cdot \left(\frac{Vp}{Vp - Vs}\right) // Rpcb \cdot \left(\frac{Vp}{Vp - Vb}\right) // Rnc \qquad \text{Eqn. 6}$$

The negative to chassis isolation resistance as measured from the propulsion bus with the stack contactors 240a-b open and the battery contactors 240c-d closed is calculated using Eqn. 7:

$$Rnc_{PB} = Rpcb \cdot \left(\frac{Vp}{Vp - Vb}\right) // Rnc \qquad \text{Eqn. 7}$$

$Rpc_{PB}$ is the apparent positive to chassis isolation resistance measured on the propulsion bus 220. $Rnc_{PB}$ is the apparent negative to chassis isolation resistance measured on the propulsion bus 220. Rpcs is the fuel cell stack 205 coolant positive to chassis isolation resistance. Rpcb is the battery positive to chassis isolation resistance and Rnc is the propulsion bus negative to chassis isolation resistance. "//" is a shorthand notation for parallel where R1/R2=1/(1/R1+1/R2). The isolation algorithm 400 from FIG. 4 will use Eqns. 5-7 and Eqn. 4 to calculate the coolant conductivity value.

The isolation algorithm 400 from FIG. 4 may need additional isolation sensors of the plurality of sensors and corresponding measurement values to calculate the coolant conductivity value 435. A third isolation value may be sensed by a third isolation sensor electrically coupled to a positive propulsion bus resistance measurement location 545a, and a second negative isolation value may include one or more negative isolation sensors electrically coupled to the negative stack isolation resistance measurement location 245b, the negative battery isolation resistance measurement location 245d, and a negative propulsion bus resistance measurement location 545b. The second negative isolation value may be the parallel resistance measurement of the negative stack isolation resistance measurement location 245b, the negative battery isolation resistance measurement location 245d, and a negative propulsion bus resistance measurement location 545b. A propulsion voltage may be sensed by a propulsion sensor electrically coupled between the positive and negative terminals of the propulsion bus 220.

The isolation algorithm 400 may add the propulsion voltage to the measurement step 415 and use the second negative isolation value in lieu of the first negative isolation value for the measurement step 425 in FIG. 4 to calculate the coolant conductivity value 435 for a multi-voltage fuel cell system 500.

Figure 6:
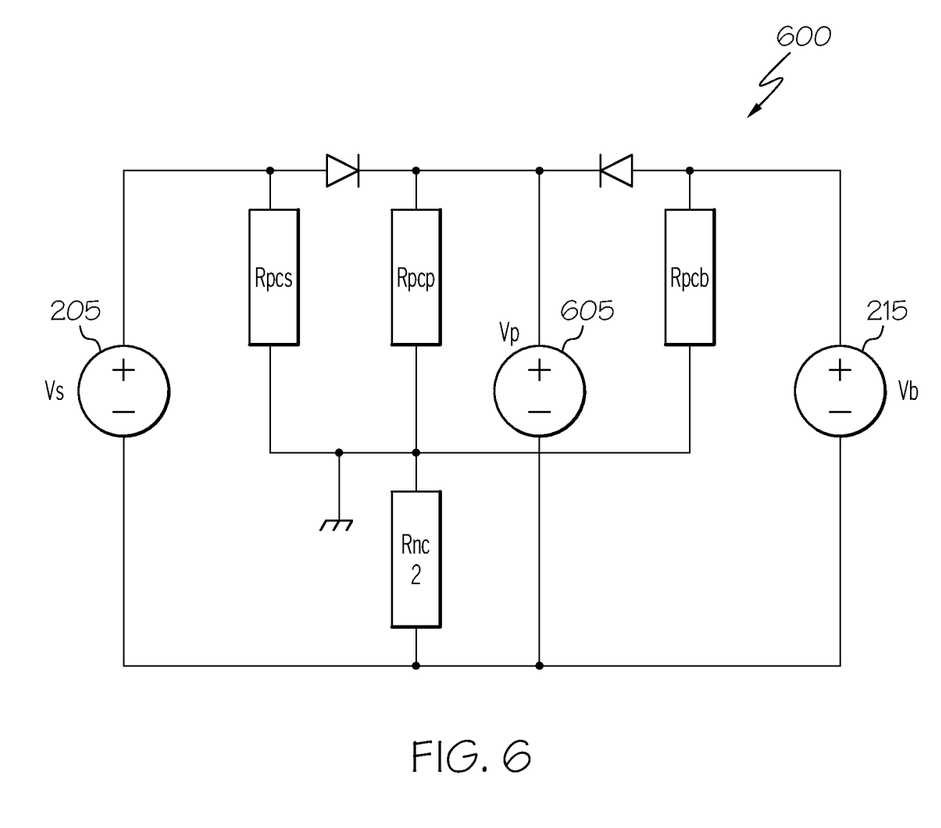
FIG. 6 depicts a multi-voltage isolation resistance model.

FIG. 6 depicts a multi-voltage isolation resistance model 600. The multi-voltage isolation resistance model 600 is another embodiment of the isolation resistance model 300 in FIG. 3. The fuel cell stack 205 voltage (Vs) and the high voltage battery 215 voltage (Vb) along with Rpcs and Rpcb are the same as found in FIG. 3. A propulsion voltage 605 (Vp) represents the electrical potential of the propulsion bus 220. Rpcp represents the isolation resistance value found of the positive propulsion bus resistance measurement location 545a. Rnc2 represents the parallel combination of all resistances connected from the shared negative terminal to ground and may include the negative stack isolation resistance measurement location 245b, the negative battery isolation resistance measurement location 245d, and negative propulsion bus resistance measurement location 545b. Rnc2 equates to the second negative isolation value.

It should be understood that the present disclosure may include any number of boost converters within the fuel cell system 200. The equations are flexible to include any number of voltages found in a bus system of the fuel cell system 200. The bus system is the system of electrical conductors used to carry electrical energy and may be usually found as a power distribution system of the vehicle 10 electrically coupling power sources (i.e. fuel cell stack 205, high voltage battery 215 for example) to electrical loads (compressor motor 225, traction motor 230, and other loads 235 for example).

The present disclosure may be embodied in hardware and/or in software (including firmware, resident software, microcode, etc.). The system controller may have at least one processor and the computer-readable medium. A computer-usable or the computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of the present disclosure may be written in a high-level programming language, such as C or C++, for development convenience. In addition, computer program code for carrying out operations of the present disclosure may also be written in other programming languages, such as, but not limited to, interpreted languages. Some modules or routines may be written in assembly language or even micro-code to enhance performance and/or memory usage. However, software embodiments of the present disclosure do not depend on implementation with a particular programming language. It will be further appreciated that the functionality of any or all of the program modules may also be implemented using discrete hardware components, one or more application specific integrated circuits (ASICs), or a programmed digital signal processor or microcontroller.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for monitoring coolant conductivity in a coolant system that is used to provide thermal management of a fuel cell stack, comprising:
    closing at least one contactor in an electrical system comprising a stack voltage and a battery voltage;
    measuring a first isolation value, a second isolation value, the stack voltage, and the battery voltage;
    opening the at least one contactor in the electrical system;
    measuring a first negative isolation value;
    calculating a stack isolation resistance using the first isolation value, the second isolation value, the first negative isolation value, the stack voltage, and the battery voltage;
    calculating a coolant conductivity value; and
    providing indicia that a coolant needs to be replaced when the coolant conductivity value crosses a threshold value.

2. The method of claim 1, wherein the at least one contactor comprises a stack contactor and a battery contactor.

3. The method of claim 2, wherein closing the at least one contactor comprises closing the stack contactor and the battery contactor and opening the at least one contactor comprises opening the stack contactor.

4. The method of claim 1, wherein an isolation algorithm comprises the steps of closing the at least one contactor, measuring the first isolation value, the second isolation value, the stack voltage, and the battery voltage, opening the at least one contactor, measuring the first isolation value, calculating the stack isolation resistance and the coolant conductivity value and providing the indicia and further comprising executing the isolation algorithm in a battery monitor controller electrically coupled to a plurality of isolation sensors, the battery monitor controller comprises a processor and a computer-readable medium and uses the isolation algorithm to calculate the coolant conductivity value.

5. The method of claim 4, wherein the plurality of isolation sensors comprises:
    a first isolation sensor electrically coupled to a positive stack isolation resistance measurement location and used to measure the first isolation value;
    a second isolation sensor electrically coupled to a positive battery isolation resistance measurement location and used to measure the second isolation value;
    a plurality of negative sensors are electrically coupled a negative stack isolation resistance measurement location, and a negative battery isolation resistance measurement location and used to measure the first negative isolation value;
    a stack sensor used to measure the stack voltage; and
    a battery sensor used to measure the battery voltage.

6. The method of claim 4, wherein measuring the first isolation value, the second isolation value, the stack voltage, and the battery voltage and further comprises measuring a third isolation value and a propulsion voltage and wherein measuring the first negative isolation value is replaced with measuring a second negative isolation value.

7. The method of claim 6, wherein the plurality of isolation sensors comprises:
    a first isolation sensor electrically coupled to a positive stack isolation resistance measurement location and used to measure the first isolation value;
    a second isolation sensor electrically coupled to a positive battery isolation resistance measurement location and used to measure the second isolation value;
    a third isolation sensor is electrically coupled to a positive propulsion bus resistance measurement location and used to measure the third isolation value;
    a plurality of negative sensors are electrically coupled to a negative stack isolation resistance measurement location, a negative battery isolation resistance measurement location, and a negative propulsion bus resistance measurement location and used to measure the second negative isolation value;
    a propulsion sensor used to measure the propulsion voltage;
    a stack sensor used to measure the stack voltage; and
    a battery sensor used to measure the battery voltage.

8. The method of claim 1, wherein a coolant conductivity sensor is not used.

9. A method of monitoring isolation resistance in a vehicular propulsion system, comprising:

circulating a coolant in a coolant system fluidly coupled to a fuel cell stack that forms at least a portion of the vehicular propulsion system wherein the coolant provides thermal management within the fuel cell stack and the coolant provides electrical isolation between the fuel cell stack and a vehicle chassis;

closing a at least one contactor in an electrical system comprising a stack voltage and a battery voltage;

measuring a first isolation value, a second isolation value, the stack voltage, and the battery voltage;

opening the at least one contactor in the electrical system;

measuring a first negative isolation value;

calculating a stack isolation resistance using the first isolation value, the second isolation value, the first negative isolation value, the stack voltage, and the battery voltage;

calculating a coolant conductivity value; and indicating the coolant in the coolant system needs to be replaced with the coolant conductivity value crosses a threshold value.

10. The method of claim 9, wherein the at least one contactor includes a stack contactor and a battery contactor.

11. The method of claim 10, wherein closing the at least one contactor comprises closing the stack contactor and the battery contactor and opening the at least one contactor comprises opening the stack contactor.

12. The method of claim 9, wherein an isolation algorithm comprises the steps of closing the at least one contactor, measuring the first isolation value, the second isolation value, the stack voltage, and the battery voltage, opening the at least one contactor, measuring the first isolation value, calculating the stack isolation resistance and the coolant conductivity value and providing an indicia and further comprising executing the isolation algorithm in a battery monitor controller electrically coupled to a plurality of isolation sensors, the battery monitor controller comprises a processor and a computer-readable medium and uses the isolation algorithm to calculate the coolant conductivity value.

13. The method of claim 12, wherein the plurality of isolation sensors comprises:
a first isolation sensor electrically coupled to a positive stack isolation resistance measurement location and used to measure the first isolation value;
a second isolation sensor electrically coupled to a positive battery isolation resistance measurement location and used to measure the second isolation value;
a plurality of negative sensors are electrically coupled to a negative stack isolation resistance measurement location, and a negative battery isolation resistance measurement location and used to measure the first negative isolation value;
a stack sensor used to measure the stack voltage; and
a battery sensor used to measure the battery voltage.

14. The method of claim 12, further comprising measuring a third isolation value and a propulsion voltage and wherein measuring the first negative isolation value is replaced with measuring a second negative isolation value.

15. The method of claim 14, wherein the plurality of isolation sensors comprises:
a first isolation sensor electrically coupled to a positive stack isolation resistance measurement location and used to measure the first isolation value;
a second isolation sensor electrically coupled to a positive battery isolation resistance measurement location and used to measure the second isolation value;
a third isolation sensor is electrically coupled to a positive propulsion bus resistance measurement location and used to measure the third isolation value;
a plurality of negative sensors are electrically coupled a negative stack isolation resistance measurement location, a negative battery isolation resistance measurement location, and a negative propulsion bus resistance measurement location and used to measure the second negative isolation value;
a propulsion sensor used to measure the propulsion voltage;
a stack sensor used to measure the stack voltage; and
a battery sensor used to measure the battery voltage.

16. The method of claim 9, wherein a coolant conductivity sensor is not used.

17. A coolant conductivity estimation system for a fuel cell, comprising:
a plurality of isolation sensors comprising:
a first isolation sensor electrically coupled to a positive stack isolation resistance measurement location and used to measure a first isolation value,
a second isolation sensor electrically coupled to a positive battery isolation resistance measurement location and used to measure a second isolation value,
a plurality of negative sensors are electrically coupled to a negative stack isolation resistance measurement location, and a negative battery isolation resistance measurement location and used to measure a first negative isolation value,
a stack sensor used to measure a stack voltage, and
a battery sensor used to measure a battery voltage; and
a battery monitor controller electrically coupled to the plurality of isolation sensors and comprising a processor and a non transitory computer-readable medium and executing an isolation algorithm, the isolation algorithm when executed causes the battery monitor controller to perform the steps of:
closing at least one contactor in an electrical system comprising the stack voltage and the battery voltage,
measuring the first isolation value, the second isolation value, the stack voltage, and the battery voltage,
opening the at least one contactor in the electrical system,
measuring the first negative isolation value,
calculating a stack isolation resistance using the first isolation value, the second isolation value, the first negative isolation value, the stack voltage, and the battery voltage,
calculating a coolant conductivity value, and
providing indicia that a coolant needs to be replaced when the coolant conductivity value crosses a threshold value.

18. The system of claim 17, further comprising measuring a third isolation value and a propulsion voltage wherein measuring the first negative isolation value is replaced with measuring a second negative isolation value.

19. The system of claim 18, wherein the plurality of isolation sensors further comprise a third isolation sensor that is electrically coupled to a positive propulsion bus resistance measurement location and used to measure the third isolation value and a negative propulsion bus resistance measurement location and used to measure the second negative isolation value.

20. The system of claim 17 wherein a coolant conductivity sensor is not used.

* * * * *